(12) United States Patent
Nelson et al.

(10) Patent No.: US 12,186,489 B2
(45) Date of Patent: Jan. 7, 2025

(54) PATIENT INTERFACE AND A SPEECH VALVE THEREFOR

(71) Applicant: Fisher & Paykel Healthcare Limited, Auckland (NZ)

(72) Inventors: Grant Leigh Nelson, Auckland (NZ); Carsten Ma On Wong Corazza, Auckland (NZ); Joseph Jules Nihotte, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/523,460

(22) Filed: Nov. 29, 2023

(65) Prior Publication Data

US 2024/0091486 A1 Mar. 21, 2024

Related U.S. Application Data

(62) Division of application No. 16/761,919, filed as application No. PCT/ZN2018/050158 on Nov. 9, 2018, now Pat. No. 11,878,124.

(Continued)

(51) Int. Cl.
*A61M 16/20* (2006.01)
*A61M 16/00* (2006.01)
(Continued)

(52) U.S. Cl.
CPC ........ *A61M 16/20* (2013.01); *A61M 16/0066* (2013.01); *A61M 16/06* (2013.01);
(Continued)

(58) Field of Classification Search
CPC .. A61M 16/00; A61M 16/0003; A61M 16/06; A61M 16/0605; A61M 16/20;
(Continued)

(56) References Cited

U.S. PATENT DOCUMENTS

| 5,411,021 A | 5/1995 | Gdulla et al. |
| 6,394,091 B1 | 5/2002 | Giorgini |

(Continued)

FOREIGN PATENT DOCUMENTS

| EP | 0566400 | 10/1993 |
| EP | 1614447 | 1/2006 |

(Continued)

OTHER PUBLICATIONS

International Preliminary Report on Patentability in Application No. PCT/NZ2018/050158, issued May 12, 2020 in 13 pages.

(Continued)

*Primary Examiner* — Colin W Stuart
(74) *Attorney, Agent, or Firm* — VIA LLP

(57) ABSTRACT

A patient interface of a respiratory therapy system is provided, and includes a mask body; a mask seal secured to the mask body and configured to form a seal with the user's face, at least around the user's mouth; the mask body and mask seal being arranged to define an interior breathing chamber of the patient interface; and an inlet to the breathing chamber configured to receive a flow of breathable gases into the breathing chamber. To assist in allowing a user to speak clearly whilst wearing/using the patient interface, a user actuatable speech valve is provided on the patient interface and is operable to selectively occlude and open a speech flow path from the breathing chamber to atmosphere when the user wishes to speak.

20 Claims, 14 Drawing Sheets

Related U.S. Application Data

(60) Provisional application No. 62/583,915, filed on Nov. 9, 2017.

(51) Int. Cl.
| | | |
|---|---|---|
| *A61M 16/06* | (2006.01) | |
| *A61M 16/08* | (2006.01) | |
| *A61M 16/16* | (2006.01) | |
| *A62B 7/08* | (2006.01) | |
| *A62B 9/00* | (2006.01) | |
| *A62B 9/02* | (2006.01) | |
| *A62B 18/02* | (2006.01) | |
| *A62B 18/10* | (2006.01) | |

(52) U.S. Cl.
CPC .... *A61M 16/0616* (2014.02); *A61M 16/0683* (2013.01); *A61M 16/0816* (2013.01); *A61M 16/0825* (2014.02); *A61M 16/16* (2013.01); *A61M 16/201* (2014.02); *A62B 7/08* (2013.01); *A62B 9/003* (2013.01); *A62B 9/02* (2013.01); *A62B 18/02* (2013.01); *A62B 18/025* (2013.01); *A62B 18/10* (2013.01); *A61M 2205/582* (2013.01)

(58) Field of Classification Search
CPC ............. A61M 16/201; A61M 16/206; A61M 16/208; A61M 16/209; A61M 16/0468; A61M 16/0816; A61M 2016/0661; A62B 9/02; A62B 9/00; A62B 18/00; A62B 18/02; A62B 18/025; A62B 18/08; A62B 18/10

See application file for complete search history.

(56) References Cited

U.S. PATENT DOCUMENTS

| | | |
|---|---|---|
| 6,513,526 B2 | 2/2003 | Kwok et al. |
| 9,839,761 B1 | 12/2017 | Rucker |
| 2012/0055471 A1 | 3/2012 | Hadas et al. |
| 2013/0139820 A1 | 6/2013 | Haibach |
| 2015/0090257 A1 | 4/2015 | Larsen |
| 2019/0083823 A1 | 3/2019 | Castiglione |
| 2020/0324150 A1 | 10/2020 | Nelson et al. |

FOREIGN PATENT DOCUMENTS

| | | |
|---|---|---|
| WO | WO 2011/077254 | 6/2011 |
| WO | WO 2012/023107 | 2/2012 |
| WO | WO 2014/111828 | 7/2014 |
| WO | WO 2017/070352 | 4/2017 |

OTHER PUBLICATIONS

International Search Report and Written Opinion in Application No. PCT/NZ2018/050158, mailed Mar. 4, 2019 in 19 pages.

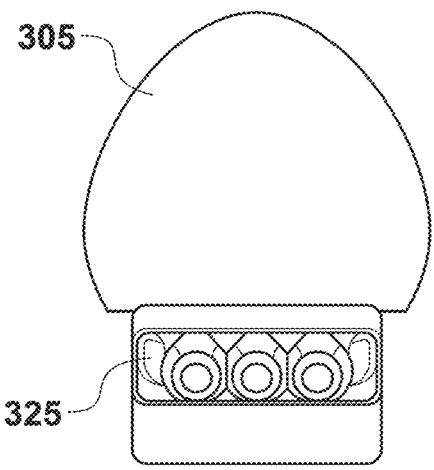
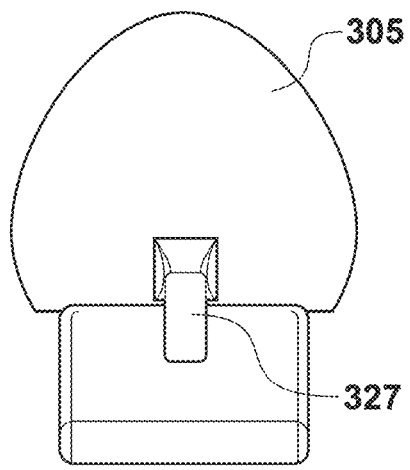
Figure 17A  Figure 17B
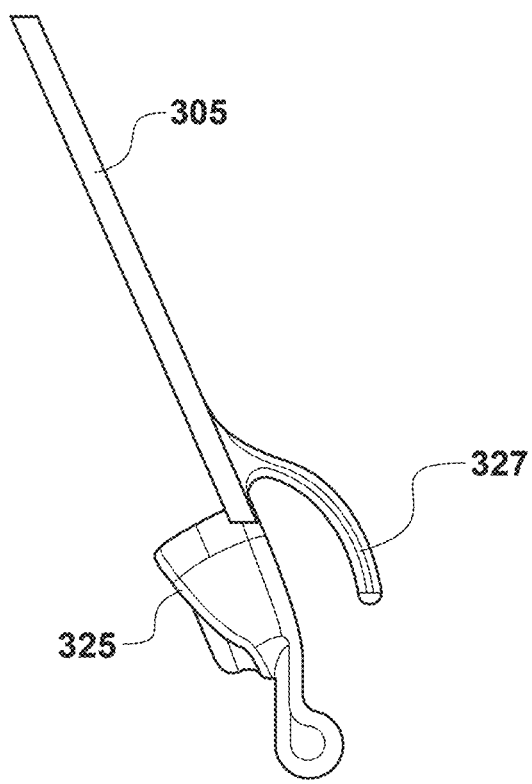
Figure 18

PATIENT INTERFACE AND A SPEECH VALVE THEREFOR

BACKGROUND OF THE DISCLOSURE

Field of the Disclosure

The present disclosure generally relates to a patient interface such as a face mask that covers at least the mouth of a user to supply respiratory gas under positive pressure. More specifically, the present invention relates to such patient interfaces and a speech valve therefor, that are configured to facilitate vocal communication by the wearer.

The present disclosure also relates to a patient interface and stethoscope listening device adapted to allow the user of the stethoscope to listen to a patient speaking while wearing the patient interface.

Description of the Related Art

Patient interfaces such as face masks can be used to provide respiratory gases at a positive pressure to a user. In configurations in which a both the mouth and a nose of a user are covered, a full face mask typically overlies the bridge of the nose, and encircles the nose and mouth of the user. In other examples an oral mask can be provided which encircles the mouth only. Such a mask typically comprises a relatively rigid mask shell comprising an inlet aperture configured to be connected to a gas delivery conduit, typically by a rotatable conduit connector. The conduit connector is typically an elbow connector. A sealing cushion, typically of relatively soft and flexible silicone or the like is secured to the more rigid mask shell, and comprises a face seal configured to contact and seal against the user's face in use. The sealing cushion may be secured to the mask shell by overmoulding for example. The sealing cushion can comprise regions of varying or different flexibility, and can sometimes comprise a movable or rolling portion that can move towards or the mask shell to adjust to the contours of the user's face.

A patient interface typically comprises a rigid mask shell and a flexible mask seal in the form of a sealing cushion. The patient interface may further comprise the conduit connector. In some cases the assembly may further comprise a rigid or semi-rigid frame to which the mask shell can be mounted, usually removeably. Headgear comprising headgear straps may be secured directly to the mask shell, or to the frame if present, to mount the mask assembly on the head of the user.

A respiratory therapy system typically delivers heated and/or humidified gases to the face mask for various medical or therapy treatments. Such a system can be configured to control any or all of temperature, humidity, pressure and flow rate of the breathable gas delivered to the patient. A respiratory therapy system is typically used for the treatment of respiratory conditions such as, for example, as obstructive sleep apnea (OSA) or chronic obstructive pulmonary disease (COPD). Such a system may be configured to generate a flow of breathable gases using a flow generator comprising a blower or the like, and/or may be configured to receive a flow of breathable gas from a separate pressurised gases source, such as a pressurised oxygen supply in a hospital.

One method of treating respiratory distress and certain respiratory disorders (including Chronic Obstructive Pulmonary Disease or COPD and Obstructive Sleep Apnea or OSA) is the provision of Continuous Positive Airway Pressure (CPAP) or other forms of Positive Airway Pressure (PAP) to support a user's respiratory system. Non-invasive respiratory pressurisation or non-invasive ventilation (NIV) is commonly administered by delivering pressurised breathing gases to a user's mouth and/or nose.

Conventional patient interfaces are configured to form a seal with the user's face or upper airway to facilitate adequate pressurisation of the user's respiratory system. Forma™ Oracle™, Zest™, Opus™ and Simplus™ are examples of sealing respiratory user interfaces produced by Fisher & Paykel Healthcare Limited. These interfaces are configured to seal with a user's face, mouth, nose and nares respectively. The seal formed between the interface and user's respiratory system allows the mask pressure to be regulated by reducing gas leaks and providing a controlled breathing gases exhaust. Gases may be exhausted from the user interface directly to the surrounding atmosphere through outlet vents or to another component in the breathing assistance system responsible for controlling the exhaust of breathing gas. For example, an expiratory limb may be provided being an expiratory gas flow path for the expiratory gas to flow from the patient interface back to the base unit. In some examples, the patient interface can be provided with an anti-asphyxia valve arrangement configured to be in a closed position when there is a flow of breathable gases from a gases source, but to be able to open when there is no flow of breathable gases into the patient interface, to allow the patient to be able to breathe even when there is no flow of breathable gases.

During the respiratory treatment, it can be a problem for users to communicate while wearing the face mask, as the mask muffles the voice. In addition, communication is hampered when the face mask is under pressurisation by a respiratory system. The positive pressure restricts the out-breath required for talking, and the direction of the airflow restricts the clarity of the talking sound. Overall, the speech of the user is muffled and the audibility is decreased during respiratory treatment.

The problems with communicating during respiratory therapy can cause reduced patient compliance with the therapy, in that a user is tempted to remove the mask before speaking. However, removing the mask to speak and then replacing and/or repositioning it correctly on the face can be difficult for the user. In addition, the removal of the mask can set off undesired alarms from the respiratory therapy system because the pressure drop and/or increase in air flow caused by the removal of the mask may be interpreted by the system as an unintentional leak. In any event, removing the mask disrupts the respiratory therapy or treatment being applied.

SUMMARY OF THE DISCLOSURE

It is an object of the present disclosure to provide a respiratory user interface which at least partially overcomes or ameliorates the abovementioned problems or disadvantages, or at least which provides the user with a useful choice.

In one aspect there is provided a patient interface configured to be connected to a respiratory therapy system to deliver a flow of breathable gases to a user, the patient interface comprising:
   a. a mask body;
   b. a mask seal secured to the mask body and configured to form a seal with the user's face, at least around the user's mouth; the mask body and mask seal being arranged to define an interior breathing chamber of the patient interface;

c. an inlet to the breathing chamber configured to receive a flow of breathable gases into the breathing chamber; and d. a user actuatable speech valve operable to selectively occlude and open a speech flow path from the breathing chamber to atmosphere when the user wishes to speak.

The speech valve may comprise a vent comprising at least one vent opening configured to be in fluid communication with the breathing chamber and the ambient environment; and a sealing member, the sealing member and vent opening being configured such that the vent opening can be selectively occluded by the sealing member. The vent may comprise a plurality of vent openings. At least one of the vent opening and the sealing member may be movable between a first position in which the sealing member sealingly occludes the vent opening, and a second position wherein the sealing member at least partially opens the vent opening.

A region of the speech valve may be accessible externally of the patient interface and operably connected to the vent opening or the sealing member, the region being accessible to the user's hand and configured to move at least one of the vent opening and the sealing member between the first and second positions. The sealing member may be movable between the first and second positions.

The patient interface may be configured to exert a bias on the speech valve to bias the speech valve to occlude the speech flow path. The speech valve, or at least a movable part thereof may be exposed to the breathing chamber such that the pressure within the breathing chamber exerts a mechanical bias on the speech valve.

The patient interface may comprise biasing means configured to exert a bias, or a further bias, on the speech valve to bias the speech valve to occlude the speech flow path, the biasing means being selected from any one or more of:

a. a mechanical biasing means;
b. a magnetic biasing means;
c. an electro-mechanical biasing means.

At least part of the speech valve may be exposed to the interior of the breathing chamber such that pressure within the breathing chamber exerts a pneumatic bias on the speech valve to bias the speech valve to occlude the speech flow path.

The at least one vent opening may be provided at the breathing gas inlet, and further wherein the patient interface comprises a conduit connector configured to connect a breathing gas delivery conduit to the breathing gas inlet, the sealing member being coupled to the conduit connector, wherein the conduit connector and the sealing member are configured to be movable relative to the breathing gas inlet to open and occlude the vent opening. The conduit connector and the sealing member may be configured to be movable in the direction of the longitudinal axis of the breathing gas inlet. The conduit connector and the sealing member may be configured to be movable by rotation about the longitudinal axis of the breathing gas inlet.

The sealing member may be positioned inside the breathing chamber. The sealing member may extend radially outwardly from a tubular part of the conduit connector that extends through the breathing gas inlet.

The conduit connector may comprise an elbow connector attached to, or configured to be attached to, a distal end of the breathing gas delivery conduit.

The inlet may comprise an inlet aperture, and the vent comprises a plurality of vent openings arranged around the perimeter of the inlet aperture.

The conduit connector and the inlet aperture may be configured to engage with any one of:

a. a friction fit;
b. a sliding fit.

The sealing member may comprise a plunger slidably located in an elongate barrel which extends into the breathing chamber, and the at least one vent opening is formed in the barrel. The vent opening comprises at least one elongate channel or groove disposed along a part of the barrel, the channel or groove extending between the ambient environment and the breathing chamber. A plurality of elongate channels or grooves may be provided.

The first position and second position may be substantially coaxial with the longitudinal axis of the barrel.

The projecting region of the speech valve may comprise a cap or button configured to be touched by the user to actuate the speech valve. The cap or button protrudes from the exterior of the patient interface when the speech valve is occluded. The cap or button may be substantially flush with the exterior of the patient interface when the speech valve is occluded.

The cap or button may be aligned with a central axis of the patient interface, when the patient interface is viewed from the front.

The direction of actuation of the speech valve may not be aligned with a longitudinal axis of the breathing gas inlet.

The speech valve may be positioned substantially adjacent the mouth of the user, when the patient interface is worn by the user.

The plunger may be in a forward position in the barrel when the valve is closed, and the plunger may be in a retracted position in which the plunger is recessed within the barrel, when the valve is open.

The plunger and the barrel may be configured to engage with any one of:

a. a friction fit;
b. a sliding fit.

The patient interface may comprise one or more mechanical biasing elements configured to exert a mechanical bias to occlude, or assist occluding, the speech valve. At least one mechanical biasing element may comprise a spring. At least one mechanical biasing element may comprise a living hinge formed integrally with the plunger or the barrel or the patient interface.

The barrel or the sealing member may comprise at least one groove, the other of the barrel and the sealing member including a longitudinal protrusion slidable along the groove as the valve is opened and occluded, wherein the groove forms the vent opening, when the valve is open.

The longitudinal axis of the or each groove may be parallel with the direction of movement of the plunger along the barrel.

A plurality of grooves may be provided.

The plunger may comprise a guide element configured to engage with a corresponding guide element on the barrel, to guide the plunger along the barrel.

An end stop may be provided configured to limit movement of the plunger within the barrel.

The sealing member may be pivotally mounted on the patient interface, pivoting of the sealing member occluding and opening the speech valve.

The sealing member may comprise a sealing lip or flange which is substantially coterminous or overlapping with a periphery of a region of the patient interface in which the speech valve is located.

The sealing member or the patient interface may comprise a pivot member connected to a pivot mount on the other of the sealing member and the patient interface. The pivot member and pivot mount may be positioned below the speech vent. The pivot mount may include a recess in which the pivot member is received and about which the pivot member can pivot. The pivot member may be integral with the sealing member.

The speech valve may be located substantially adjacent the mouth of the user when the patient interface is mounted on the user. The speech valve may be in direct fluid communication with the breathing gas inlet of the patient interface. The speech valve may be configured such that the supply of breathable gas entering the patient interface through the inlet acts on the sealing member to bias the sealing member to a closed position. The speech valve may be configured such that when the speech valve is open, the sealing member restricts the flow of breathable gas through the breathing gas inlet.

The protruding region of the speech valve may project from the sealing member and extends from the interior of the patient interface through a cut-out in the patient interface, the protrusion being spaced from the pivot. The protruding region may be integrally formed with the sealing member. The protruding region may comprise a textured or uneven outer surface.

The mechanical biasing means may comprise a living spring being an elastically deformable projection integrally formed with the sealing member, the living hinge being in contact with the interior of the patient interface.

The speech valve may comprise a single vent opening. The single vent opening may be positioned adjacent to, and above, the breathing gas inlet, when the patient interface is viewed from the front.

The speech valve may comprise a plurality of vent openings. The plurality of vent openings may be arranged on the patient interface in an array of at least one row and/or column of vent openings, multiple vent openings being in each row and/or column. A plurality of rows and/or columns of vent openings may be provided.

The patient interface may be any one of:
  a. an oral mask configured to seal around the mouth of the patient; or
  b. a full face mask configured to seal around both the mouth and nose of the patient.

According to another aspect of the disclosure, there is provided a patient interface configured to be connected to a respiratory therapy system to deliver a flow of breathable gases to a user, the patient interface comprising:
  a. a mask body;
  b. a mask seal secured to the mask body and configured to form a seal with the user's face, at least around the user's mouth; the mask body and mask seal being arranged to define an interior breathing chamber of the patient interface;
  c. an inlet port to the breathing chamber configured to receive a flow of breathable gases into the breathing chamber; and
  d. a user actuated speech valve operable to selectively open a flow path from the breathing chamber to atmosphere when the user wishes to speak; wherein
  e. the speech valve comprises at least one vent, and a sealing member mounted on a conduit connector that projects through the inlet into the breathing chamber, movement of the conduit connector moving the sealing member to selectively occlude and open the vent with the sealing member.

According to another aspect of the disclosure, there is provided a patient interface configured to be connected to a respiratory therapy system to deliver a flow of breathable gases to a user, the patient interface comprising:
  a. a mask body;
  b. a mask seal secured to the mask body and configured to form a seal with the user's face, at least around the user's mouth; the mask body and mask seal being arranged to define an interior breathing chamber of the patient interface;
  c. an inlet port to the breathing chamber configured to receive a flow of breathable gases into the breathing chamber; and
  d. a user actuated speech valve operable to selectively open a flow path from the breathing chamber to atmosphere when the user wishes to speak; wherein
  e. the speech valve comprises a vent comprising a channel or groove provided in the inlet port and a plunger movably mounted in the inlet port so as to selectively occlude and open the channel or groove.

According to a further aspect of the disclosure, there is provided a patient interface configured to be connected to a respiratory therapy system to deliver a flow of breathable gases to a user, the patient interface comprising:
  a. a mask body;
  b. a mask seal secured to the mask body and configured to form a seal with the user's face, at least around the user's mouth; the mask body and mask seal being arranged to define an interior breathing chamber of the patient interface;
  c. an inlet port to the breathing chamber configured to receive a flow of breathable gases into the breathing chamber; and
  d. a user actuated speech valve operable to selectively open a flow path from the breathing chamber to atmosphere when the user wishes to speak; wherein
  e. the speech valve comprises at least one vent opening, and a valve flap movably mounted in the breathing chamber so as to selectively occlude and open the vent opening.

According to another aspect of the disclosure, there is provided a patient interface configured to be connected to a respiratory therapy system to deliver a flow of breathable gases to a user, the patient interface comprising:
  a. a mask body;
  b. a mask seal secured to the mask body and configured to form a seal with the user's face, at least around the user's mouth; the mask body and mask seal being arranged to define an interior breathing chamber of the patient interface;
  c. an inlet port to the breathing chamber configured to receive a flow of breathable gases into the breathing chamber; and
  d. a user actuated speech valve operable to selectively open a flow path from the breathing chamber to atmosphere when the user wishes to speak; wherein the speech valve is exposed to pressure within the breathing chamber which exerts a pneumatic bias to occlude the speech valve.

The patient interface may comprise at least one of:
  a. A gas wash-out valve configured to allow exhaled gas to exit the breathing chamber in normal use of the patient interface;
  b. An anti-asphyxia valve configured to allow the user to breathe, when breathing gases are not flowing through the inlet.

According to a further aspect of the disclosure, there is provided a patient interface assembly comprising the patient interface of any one of the above statements, and further comprising any one of:
a. an elbow connector configured to connect a gas delivery conduit to a patient interface;
b. a gas delivery conduit;
c. a gas delivery conduit connector configured to connect a gas delivery conduit to another component of the respiratory therapy system;
d. a frame configured to connect the mask body to headgear,
e. headgear configured to mount the patient interface on a user's head.

According to a further aspect of the disclosure, there is provided a respiratory therapy system comprising the patient interface, or the patient interface assembly, of any one of the above statements, and any one or more of:
a. a breathing gas flow generator;
b. a breathing gas humidifier; and/or
c. a gas delivery conduit, which may or may not be heated.

According to another aspect of the disclosure, there is provided a stethoscope device for use with a stethoscope, configured to be applied to an external surface of a patient interface of the type configured to be connected to a respiratory therapy system to deliver a flow of breathable gases to a user, where the patient interface comprises:
a mask shell;
a sealing cushion secured to the mask shell and configured to form a seal with the user's face, at least around the user's mouth; the mask shell and sealing cushion being arranged to define an interior of the patient interface;
an inlet port configured to receive a conduit for supplying a flow of breathable gases into the interior of the mask assembly though a conduit from a flow generator;
wherein the stethoscope device comprises a spacer configured to be positioned between the stethoscope and the patient interface and comprising a body having a first surface arranged to contact an exterior surface of the patient interface, and a second opposing surface arranged to contact a diaphragm of the stethoscope, the spacer body being deformable so as to:
conform to the shape of the exterior surface of the patient interface; and
attenuate or alleviate vibrations of the patient interface from being transferred through the spacer to the stethoscope.

The spacer may:
a. include a central opening defining an air gap configured to be arranged between the patient interface and stethoscope;
b. be at least partially formed from a foam material;
c. be configured to be attached to the stethoscope;
d. be configured to be attached to the patient interface.

According to another aspect of the disclosure, there is provided a patient interface including the spacer of any one of the above statements.

According to another aspect of the disclosure, there is provided a stethoscope including the spacer of any one of the above statements.

According to another aspect of the disclosure, there is provided a patient interface assembly configured to supply a positive pressure respiratory therapy to a user, including a breathable gas inlet port configured to receive a flow of breathable gases into the interior of the patient interface assembly though a conduit, the patient interface assembly including a speech valve comprising:
a. a speech valve located in the assembly comprising one or more vent openings in fluid communication between a breathing chamber of the patient interface assembly and the ambient environment;
b. a sealing member configured to be selectively movable by the user between a first position and a second position;
c. wherein when the sealing member is in the first position, the sealing member occludes the one or more openings to prevent or restrict the fluid communication through the one or more vent openings;
d. and wherein when the sealing member is in the second position, the sealing member at least partially opens the one or more vent openings to allow the flow of breathable gases through the speech valve;
e. at least part of the speech valve being located on an exterior side of the patient interface assembly and accessible to the user, such that the user can at least open the speech valve.

BRIEF DESCRIPTION OF THE DRAWINGS

A number of embodiments of the disclosure will now be described by way of example with reference to the drawings in which:

FIGS. 17a and 17b are front and rear views of a sealing element of the speech valve of FIG. 14.

FIG. 18 is a side view of the sealing element of FIG. 17.

DETAILED DESCRIPTION

Figure 1:
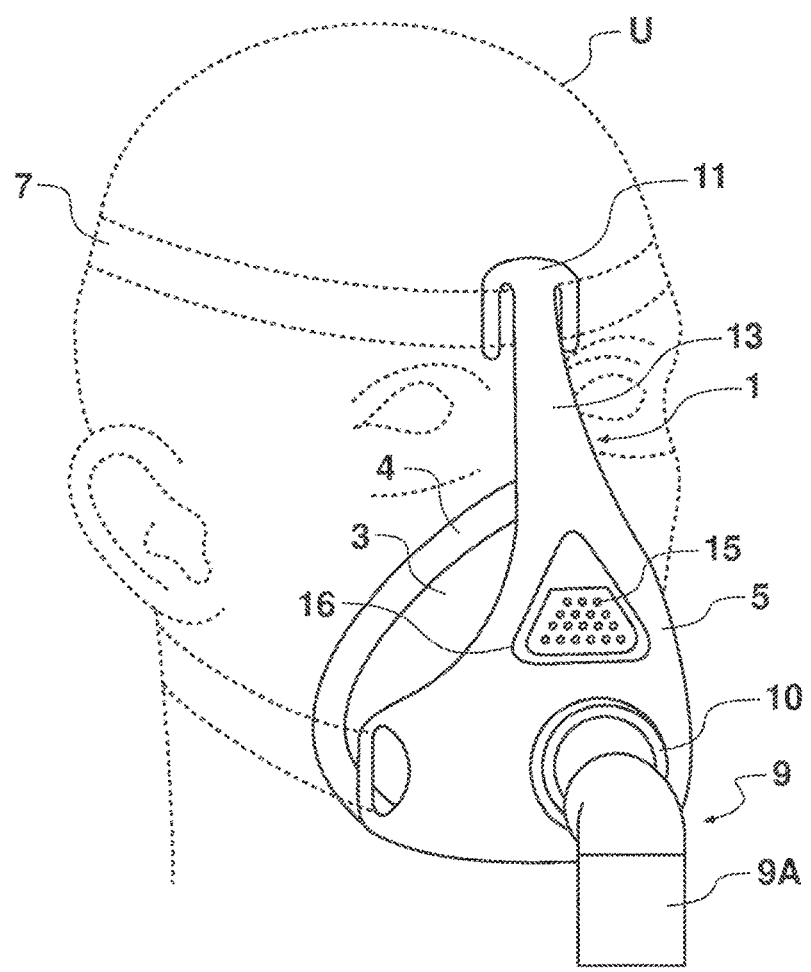
FIG. 1 is a perspective view of a patient interface assembly according to the prior art.
Figure 2:
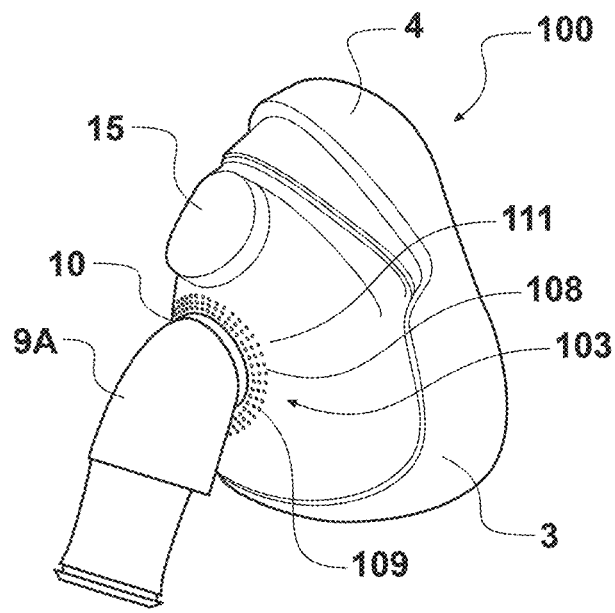
FIG. 2 is a perspective view of a patient interface assembly in accordance with a first aspect of the disclosure.
Figure 3:
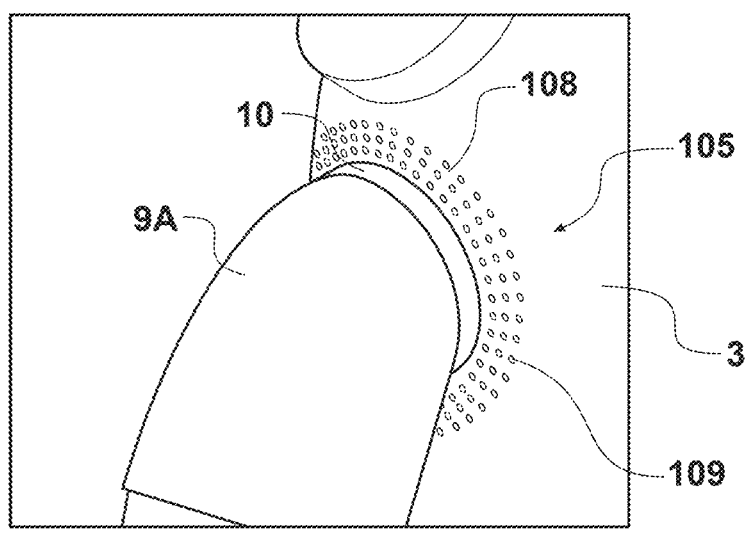
FIG. 3 is an enlarged perspective view of the assembly of FIG. 2.
Figure 4:
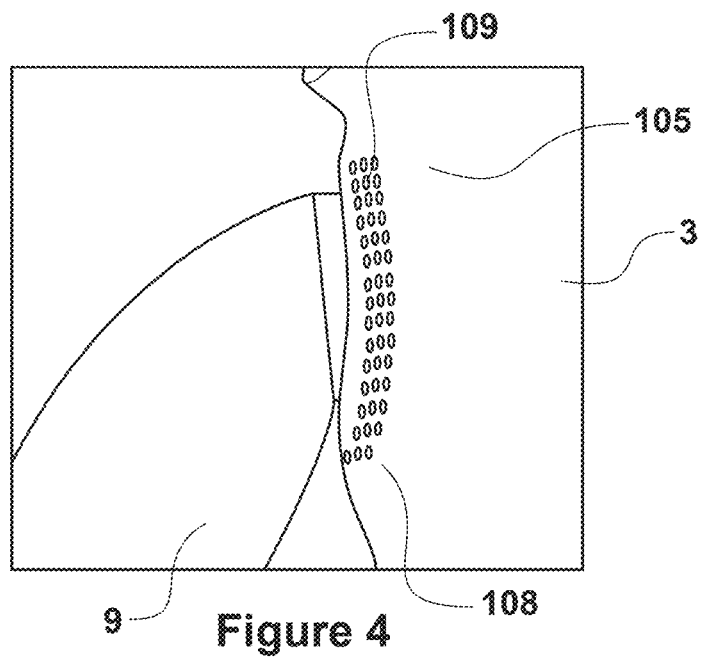
FIG. 4 is an enlarged side view of the assembly of FIGS. 2 and 3.
Figure 5:
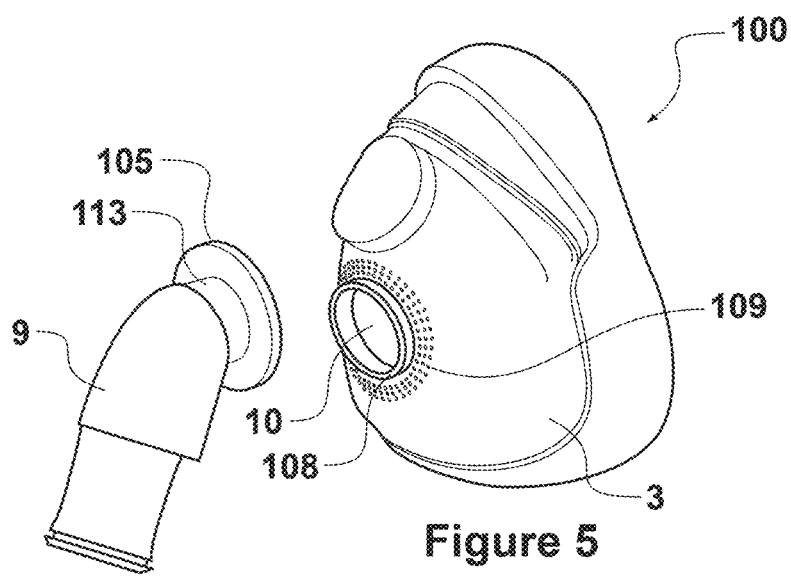
FIG. 5 is an exploded perspective view of the assembly of FIGS. 2 to 4.
Figure 6A:
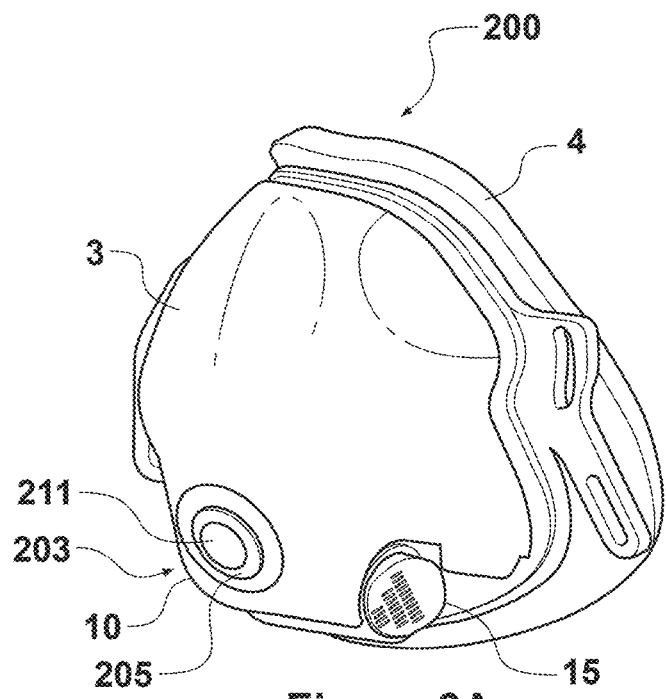
FIGS. 6a and 6b are perspective views of a patient interface assembly in accordance with a second aspect of the disclosure with a speech valve in closed and open conditions respectively.
Figure 6B:
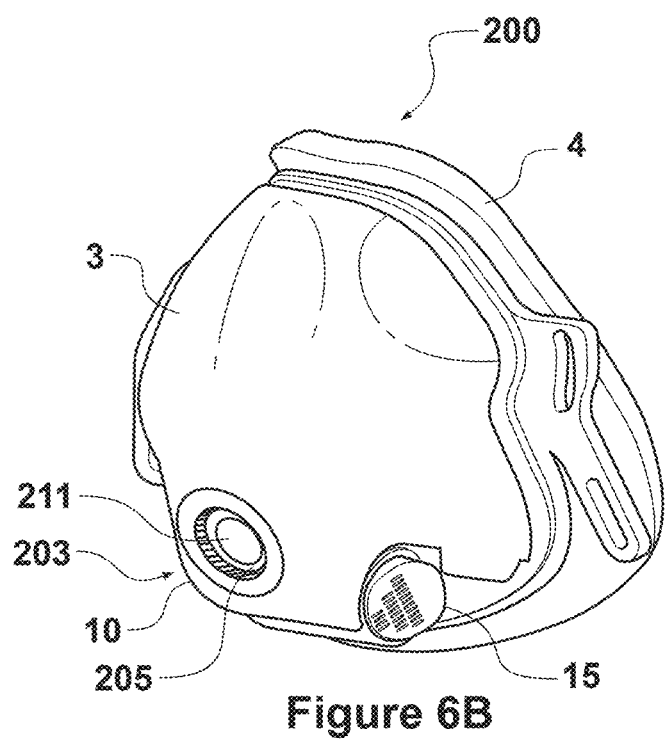
Figure 7:
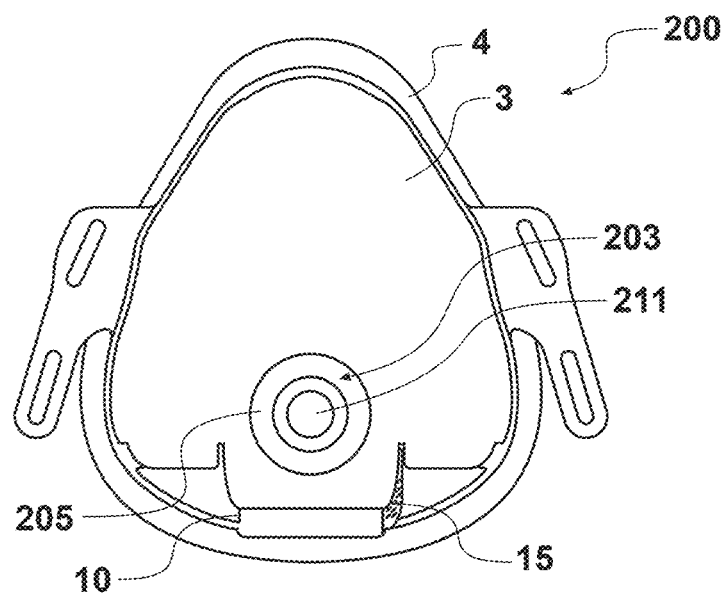
FIGS. 7 and 8 are front and rear views of the assembly of FIG. 6.
Figure 8:
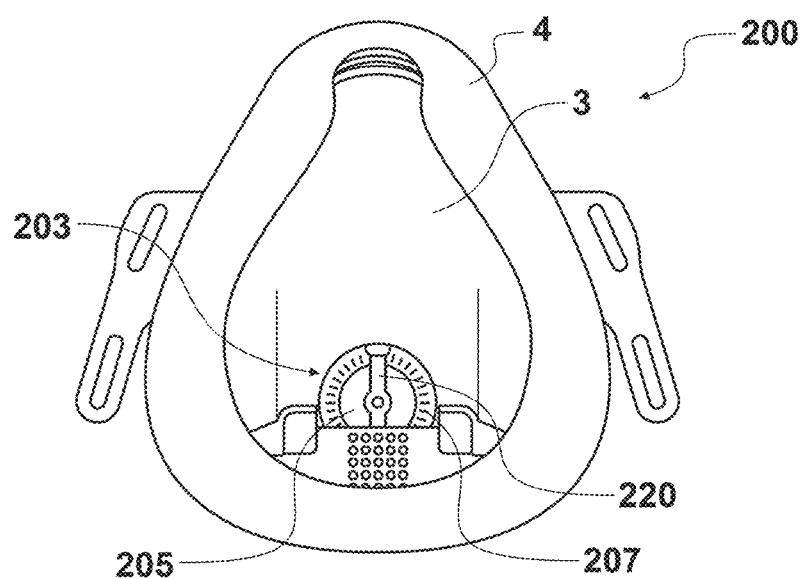
Figure 9:
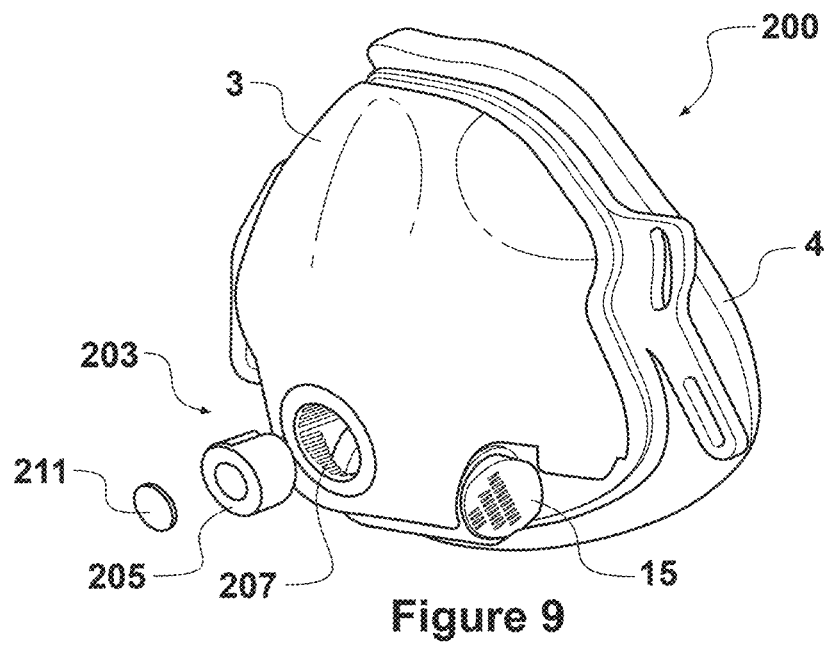
FIG. 9 is a perspective, partially exploded view of the assembly of FIGS. 6 to 8.
Figures 10A, 10B:
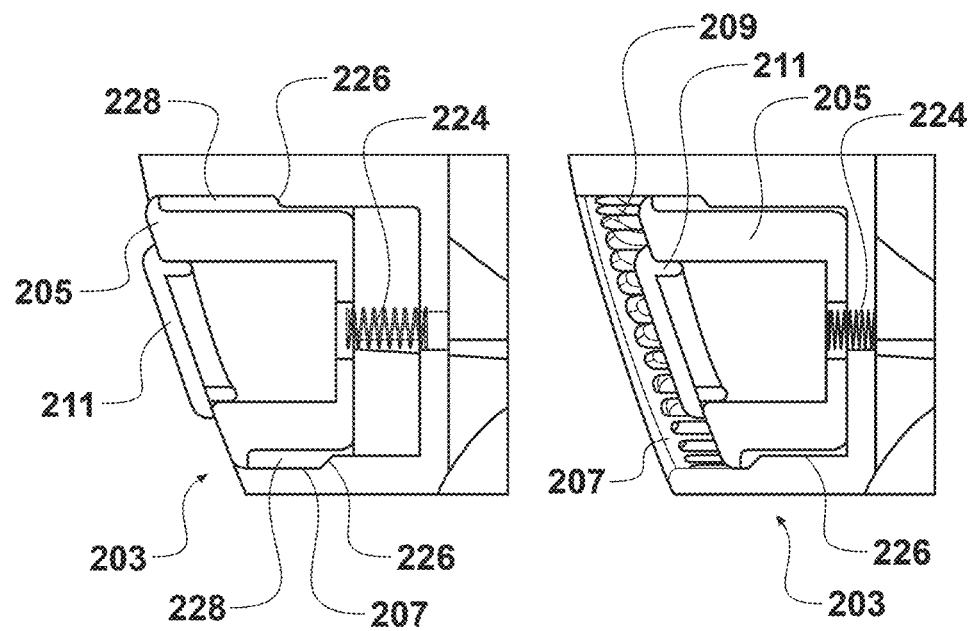
FIGS. 10a and 10b are enlarged side views of the speech valve of the assembly of FIGS. 6 to 9.
Figure 11:
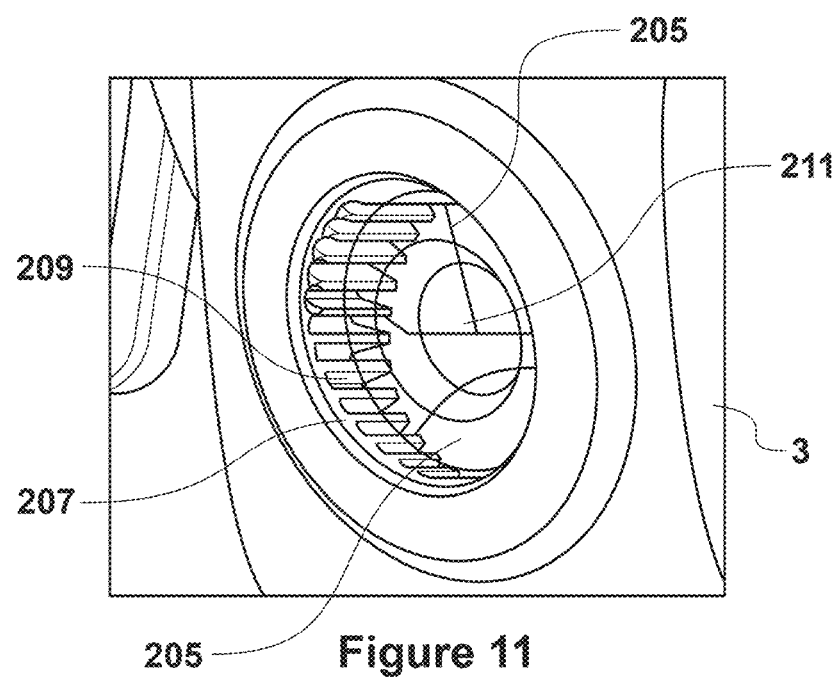
FIG. 11 is an enlarged perspective view of the speech valve of FIG. 10, in an open condition.
Figure 12:
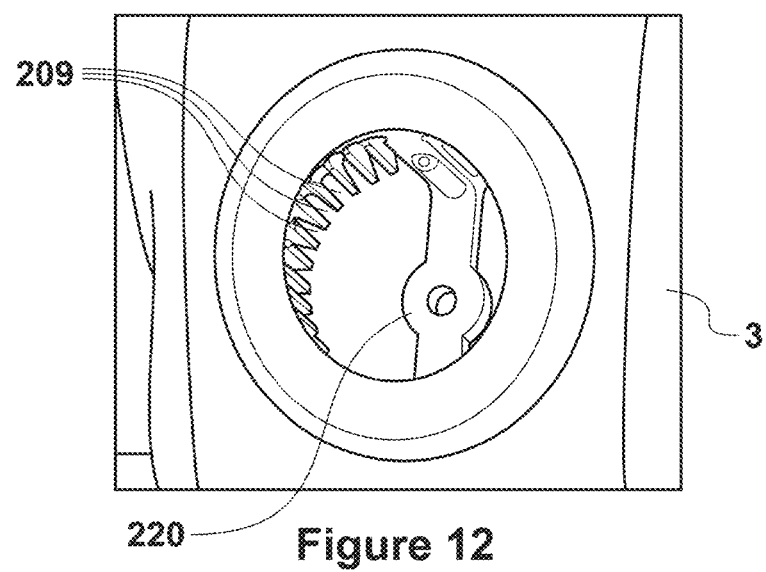
FIG. 12 is an enlarged perspective view of the speech valve of FIGS. 10 and 11, with part of the valve removed.
Figure 13:
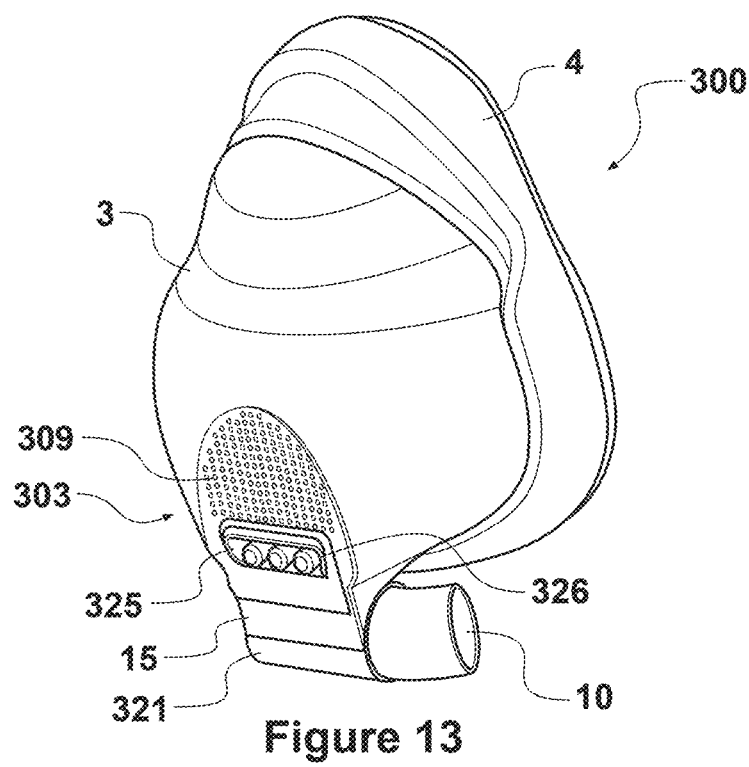
FIG. 13 is a perspective view of a patient interface assembly in accordance with a third aspect of the disclosure.
Figure 14:
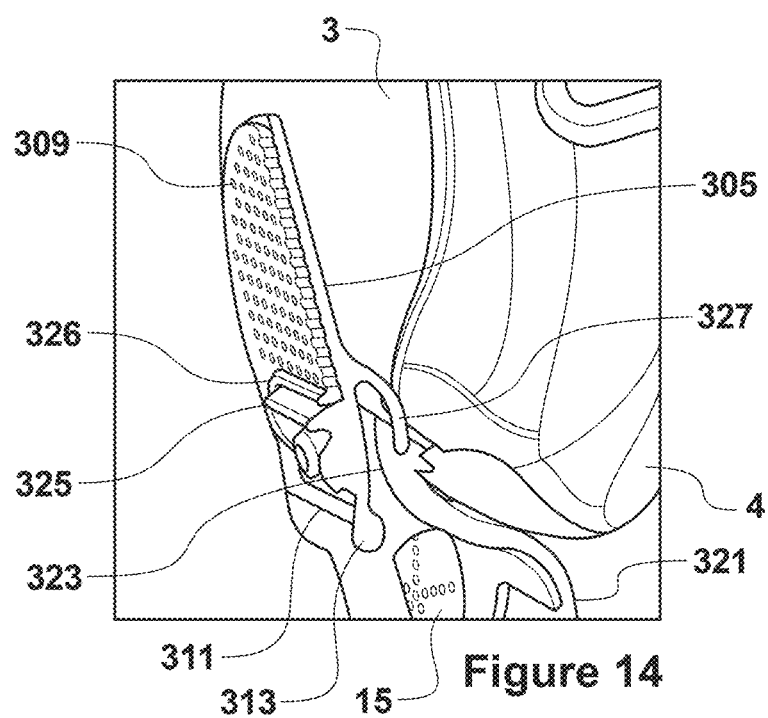
FIG. 14 is an enlarged cross-sectional perspective view of a speech valve of the assembly of FIG. 13.
Figure 15:
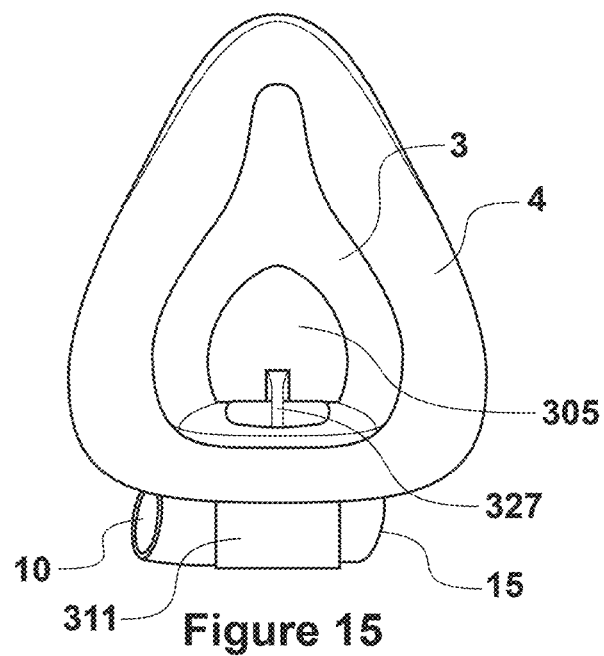
FIGS. 15 and 16 are rear and cross-sectional side views of the assembly of FIGS. 13 and 14.
Figure 16:
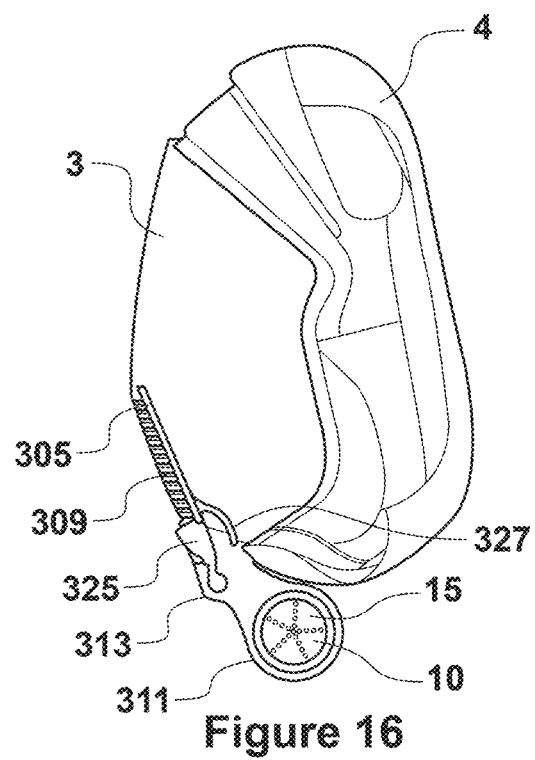

With reference initially to FIG. 1, a typical patient interface 1 is illustrated on a user U. The interface 1 can be used in the field of respiratory therapy and therefore in any respiratory treatment, respiratory assistance, resuscitation or ventilation system. In some embodiments, the interface 1 has particular utility with forms of positive pressure respiratory therapy. For example, the interface 1 can be used for administering continuous positive airway pressure ("CPAP") treatments, variable positive airway pressure ("VPAP") treatments and/or bi-level positive airway pressure ("BiPAP") treatments. The interface 1 can be compatible with one or more different types of suitable CPAP systems.

The interface 1 can comprise any of a plurality of different types of suitable mask configurations. For example, certain features, aspects and advantages of the present invention can be utilized with nasal masks, full face masks, oronasal masks or any other positive pressure mask that seals around the mouth of the user. Although the illustrated patient interfaces are full face masks, the scope of the present disclosure should not be limited by the particular embodiments described.

In the illustrated configuration, the interface 1 comprises a mask body or shell 3, a mask frame 5 and a connection port assembly 9. The mask body 3 is connected to a flexible mask seal 4 configured to cover the user's mouth and/or nose to deliver respiratory gases to the user. The mask body and the mask seal together form and define a breathing chamber into which breathable gas is delivered, from the gas source. The mask seal may be of a silicone or other flexible material that conforms to, and seals with, the user's face. The mask seal may be overmoulded to the mask body 3. The mask body in the illustrated configuration is formed of a relatively rigid material. However, in other configurations, the mask body may be flexible. In these configurations, the mask body may be of a similar material to the mask seal and may have a unitary configuration with the mask seal. The mask body 3 comprises a breathing gas inlet 10 configured to receive breathing gas from a gas supply conduit via the connection port assembly 9. The breathing gas inlet may be any suitable shape but in the described embodiments is circular.

The mask body 3 can be secured to the mask frame 5, or may be integral with the mask frame 5. The mask frame 5 is held in place on a user by a headgear assembly 7 that extends around a part or parts of the user's head. At a first end, the connection port assembly 9 can be connected to the mask body 3 and/or mask frame 5. This may be a fixed or releasable connection. In some configurations, the connection port assembly 9 can include a ball joint or other type of rotatable or swivel connector at its first end to connect to the mask body 3 and/or mask frame 5. At a second end, the connection port assembly 9 connects to a conduit that delivers breathing gas, optionally via a rotatable or swivel connector provided at the end of the connection port assembly. These type of rotatable or swivel connectors improve flexibility and comfort for the user of the mask. The connection port assembly 9 in this example comprises an elbow connector 9A configured to be connected between the mask body 3 and/or mask frame 5 and a breathing gas delivery conduit (not shown).

The mask frame 5 can couple to the mask body 3 and help stabilize the interface 1 on the user's face. The mask frame 5 can be attached to the mask body 3 with interlocking clips, tabs or other functional couplers. The mask frame 5 can be rigid, substantially rigid or semi-rigid to provide support for the mask body 3. For example, the mask frame 5 can be at least partially made of a metal or rigid plastic, such as acrylic, polycarbonate or high-density polyethylene. In other embodiments, the mask frame 5 can be omitted, and the mask body connected directly to the headgear 7.

A typical method of passively venting carbon dioxide ($CO_2$) and expiratory gases from the patient interface is via the use of a gas wash-out vent comprising a vent hole or a vent hole array that is incorporated into the mask body 3 or gas path componentry that, for example, is directly connected to the mask. In the embodiment illustrated in FIG. 1, the interface 1 has a gas wash-out vent 15 for expelling gases from inside the breathing chamber of the mask to the environment. The gas wash-out vent 15 can help expel carbon dioxide gases that are exhaled from the user to reduce the rebreathing of the carbon dioxide gases. In other embodiments, the gas wash-out vent 15 may be provided in the connection port assembly 9, for example on the elbow connector, or around or adjacent the breathing gas inlet 10.

Further, an anti-asphyxia valve may be incorporated in the patient interface, either in the mask body 3 or in the connection port assembly 9, which valve remains shut when there is a breathable gas flow into the mask body 3 through the inlet 10, but which opens to the ambient environment in the event the gas flow stops.

With reference to FIGS. 2-21, and 24, there are provided a number of embodiments of the present disclosure of a patient interface comprising a valve, or an additional valve, being a user actuated speech valve configured to selectively open a flow path from the breathing chamber to atmosphere when the user wishes to speak. The speech valve may be the sole valve provided on the patient interface, or may be provided in addition to a gas washout valve, and/or an anti-asphyxia valve as described above.

Various embodiments are described in which the speech valve includes a vent that at least in part defines the flow path, the vent comprising at least one vent opening in fluid communication between an interior of the patient interface and the ambient environment. The speech valve also comprises a sealing member. The sealing member is configured to open and close the vent opening. The speech valve is configured such that when the user wishes to speak, the user actuates the speech valve to open the vent opening. Opening the vent opens the breathing chamber to atmosphere, preferably in the region of the user's mouth, and in line with the direction of speech, and may reduce the pressure in the breathing chamber formed by the mask body and mask seal. With the valve open, the patient is able to speak with greater ease and/or clarity and is thus able to communicate more easily with clinicians, while still wearing the patient interface and without terminating the therapy. Thus the user is able to speak when required, whilst retaining all or at least some of the benefits of the therapy.

The speech valve is configured to be actuated selectively by the user, when they wish to speak. The speech valve is separate from any other venting or valve arrangement that may be provided, such as the carbon dioxide vent 15 or the anti-asphyxia valve.

With reference to FIGS. 2 to 5, and 24, a patient interface 100 in accordance with a first aspect of this disclosure has many of the features of interface 1 described above, with like features being given like references. Interface 100 comprises a full-face mask configured to seal around the user's nose and mouth.

Interface 100 comprises a speech valve 103 which is in addition to, and separate from, any exhaust or exhalation, or anti-asphyxia valve that may be provided. With reference to FIG. 24, speech valve 103 is configured, when selectively opened by the user, for example as shown in FIG. 24*b*, to open a flow path from the breathing chamber to atmosphere. This allows pressurised air to escape the breathing chamber and may reduce the pressure in the breathing chamber. In this configuration, the direction of sound waves exiting the user's mouth is similar to the direction that the pressurized air travels out of the breathing chamber. The speech valve 103 is positioned centrally on the patient interface when viewed from the front. The valve 103 is also positioned in front of the user's mouth, when viewed from both the front and side. Consequently, both the sound waves and the pressurised air exit the breathing chamber approximately in line with, and directly in front of the user's mouth. The user's speech may therefore be transferred more clearly and easily whilst still wearing the patient interface, and without terminating the therapy.

The speech valve 103 is provided in this embodiment on the mask body 3. The speech valve 103 could alternatively be provided on the mask frame 5. The speech valve 103 comprises a valve body 108 being the region of the mask body 3 surrounding the gas inlet 10, and a sealing member 105. The valve body 108 comprises a plurality of speech vent apertures or openings 109 which are arranged in an array around the inlet 10. The openings 109 together define a flow path from the inside of the breathing chamber to atmosphere. The sealing member in this example comprises a sealing disc 105. The sealing member comprises a pad which may be of a soft material such as silicone, foam, or other conformable/deformable material. The sealing member is mounted on a tubular part 113 of the conduit connector assembly 9 that projects through the inlet 10 into the interior of the mask body 3. The tubular part 113 is movable through the inlet 10 in a direction substantially aligned with the longitudinal axis of the inlet 10. The sealing disc 105 is substantially planar, and is disposed perpendicular to the axis of the inlet 10 such that the disc 105 projects radially outwardly from the tubular part 113. In one embodiment, the tubular part 113 engages with the inlet via a friction fit. In other embodiments, the tubular part 113 may have a clearance enabling it to slide freely, with the internal pressure in the breathing chamber providing a pneumatic bias which forces the sealing disk 105 against the valve body 108.

Figure 24A:
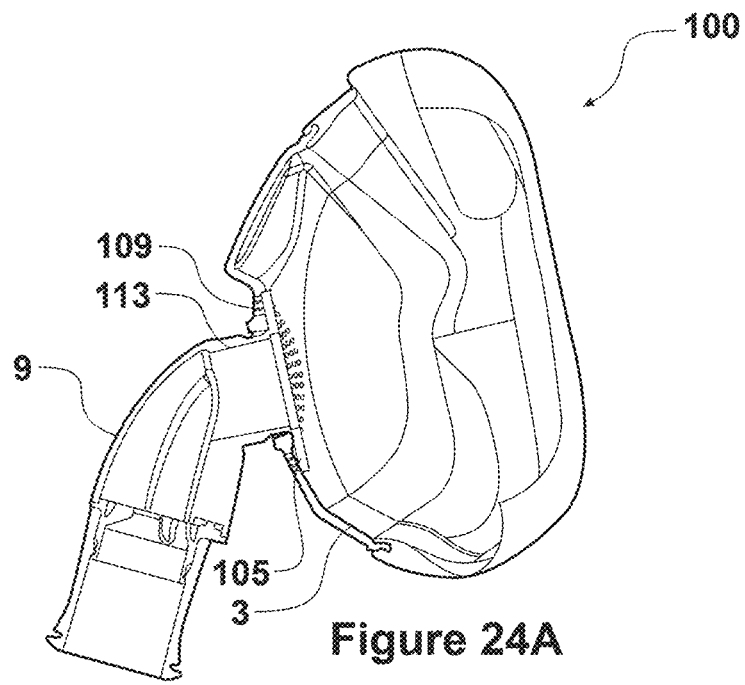
FIGS. 24a and 24b are enlarged sectional side views of the assembly of FIGS. 2 to 5, respectively showing a speech valve in a closed configuration and an open configuration.
Figure 24B:
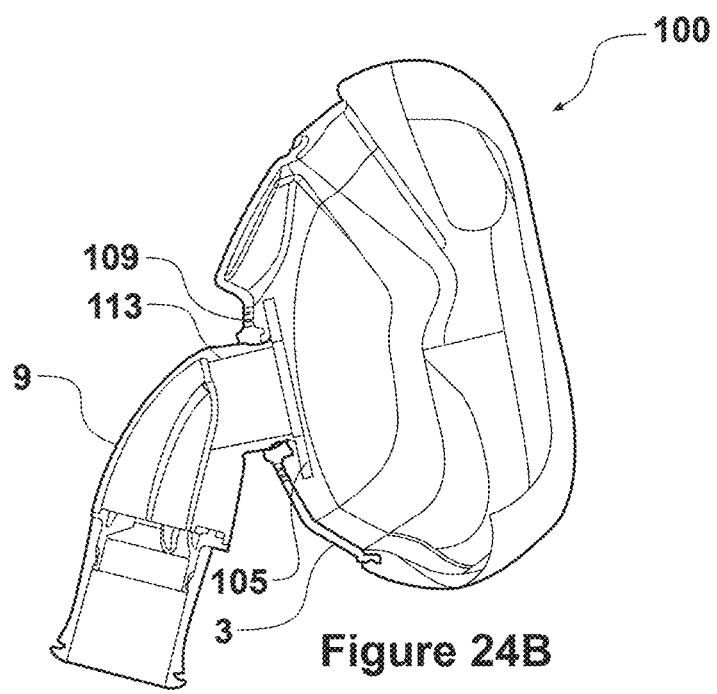

By sliding the tubular part 113 through the inlet 10, the sealing disc 105 can be moved between an open condition, for example as shown in FIG. 24*b*, in which the disc 105 is spaced from the speech vent openings 109, to a closed condition, for example as shown in FIG. 24*a*, in which the sealing disc 105 contacts the inner surface of the mask body and occludes the vent openings 109. This movement between the open and closed positions is effected by the patient gripping an exterior part of the connector assembly 9 and pushing and pulling the tubular part 113 into and out of the mask body 3. This movement is relatively natural because when the user wishes to speak a natural reaction is for the user to raise their hand to the patient interface 100 to remove the patient interface 100 to allow them to speak. When the connector assembly 9 is pressed towards the mask body 3, the sealing disc 105 is moved distally away from the interior surface of the mask body 3 which unblocks the speech valve openings 109 and allows pressurized air from the mask body 3 to escape to atmosphere. The movable connector assembly 9 thus functions as a speech valve actuator in this embodiment.

With reference to FIGS. 6 to 12, a patient interface 200 comprises a speech valve 203 comprising a sealing member comprising a plunger 205, which can be moved along a longitudinal axis within a valve body comprising an elongate barrel 207. In the illustrated embodiment, the plunger and barrel are substantially cylindrical. The speech valve 203 is centrally located towards the bottom of the mask body 3.

Barrel 207 projects into the interior of the mask body 3 and may be a separate component, or formed integrally with the mask body 3. In this example, the breathable gas inlet 10 is below the speech valve 203 and substantially perpendicular to the speech valve 203. The gas inlet 10 comprises an aperture at one end of an inlet manifold being a hollow tubular manifold, below the speech valve 203, and located at the base of the breathing chamber. A gas wash-out vent 15 is located at the opposite end of the hollow tubular manifold. In this embodiment, the patient interface 200 therefore comprises a speech valve 203 and a gas wash-out valve 15.

The barrel 207 includes a plurality of longitudinal channels or grooves 209 radially disposed around the interior surface of the barrel 207. The channels 209 extend along a substantial portion of the length of the barrel 207 and are in fluid communication with the interior of the mask body 3. The channels 209 are defined by spaced apart ribs. The channels (and ribs) extend parallel to the to the longitudinal axis of the valve body and elongate barrel. The channels 209 thus comprise speech valve openings as described above. The plunger 205 is substantially cylindrical and has a closed end, provided in this example by a plunger cap 211 located at the exterior end of the plunger 205. The plunger cap 211 may include a textured or otherwise uneven tactile-featured outer surface which is touched by the user when they wish to open the speech valve 203. The plunger cap 211 may be integral with the plunger 205 or a separate component.

When the plunger 205 is in a forward position in the barrel 207, the outer surface of the plunger 205 forms an air-tight seal with the inner surface of the barrel 207, such that the speech valve 203 is in a substantially closed condition where gas cannot flow along the channels 209. When the plunger 205 is in a retracted position, pushed into the barrel 207, and the forward part of the plunger 205 is behind the forward end of the channels 209, the ambient environment is in fluid communication with the interior of the mask body 3 via the channels 209. The valve 203 is thus in an open condition in which there is flow path from the breathing chamber to atmosphere. This may result in the pressure in the interior of the mask body 3 being reduced. With the valve 203 in the open condition, the patient is able to speak with greater clarity and ease.

The plunger 205 and the barrel 207 may be configured to have a friction fit such that the user needs to apply sufficient force to overcome the friction to press the plunger 205 into the mask body 3 to open the speech valve 203. In other embodiments the plunger may be mounted freely within the barrel 207.

The speech valve 203 further comprises a support member 220 located at an inner end of the barrel 207, inside the mask body 3. The support member 220 functions as a mount for a bias between the support member 220 and the barrel 207 which biases the speech valve 203 to the closed condition. The bias may comprise any suitable spring, such as a helical spring 224 or living spring. In the latter example the living spring may be integrally formed with either the plunger 205 or the support member 220. This mechanical bias can supplement the pneumatic bias provided by the internal gas pressure in the breathing chamber. The pneumatic bias provides the primary biasing, with the mechanical bias providing a secondary bias.

The plunger 205 may be retained within the barrel 207 by connection to the biasing means. In other forms, a retaining ring or similar could be provided at the exterior of the mask body 3 to retain the plunger within the barrel. Alternatively, the plunger 205 and barrel 207 may be provided with an end stop feature comprising a protrusion formed on one component which engages with a recess on the other to prevent the plunger 205 from being fully removed from the barrel 207.

The barrel 207 includes two plunger guides, each comprising an elongate rib 226 on the interior of the barrel 207 which each mate with a respective complementary elongate slot 228 on the outer surface of the plunger 205, to orientate and guide the plunger 205 relative to the barrel 207.

The speech valve 203 is mounted in the mask body 3 such that the front of the valve 203, namely the front of the plunger 205 plunger cap 211 is substantially flush with the exterior outer surface of the mask body 3. In this embodiment, if a user rolls their head or brushes the patient interface 200 against an object (e.g. a pillow, bedding) or something contacts the front of the patient interface 200 accidentally, the likelihood of accidental or unintentional retraction or depression of the plunger 205 and opening of the speech valve 203 is reduced.

In use, during respiratory therapy, when the user wishes to speak more clearly and easily the user can open the speech valve 203 by pressing the plunger cap 211 towards their face using their finger. As discussed above, raising their hand to the patient interface 200 is a natural inclination of most users when wanting to speak in any case. The positive pressure on the interior of the patient interface 200, in combination with any frictional resistance between the plunger 205 and barrel 207, resists the plunger 205 being pressed inward, so the user must press with a sufficient force to overcome this pressure. The force of any biasing means must also be overcome for the user to open the valve 203. In some embodiments, the pneumatic pressure caused by the pressure in the breathing chamber may be sufficient to sealing close the speech valve 203.

When the plunger 205 is in a retracted condition and the channels 209 are in fluid communication with the ambient environment such that the valve 203 is open, the positive pressure inside the patient interface 100 causes breathing gases to flow out of the interior of the mask body 3 through the channels 214.

The flow rate of the speech valve 203 when the plunger 205 is retracted may be up to about 60 litres per minute or may be up to about 50 litres per minute or may be up to about 40 litres per minute or may be up to about 30 litres per minute or may be up to about 20 litres per minute or may be up to about 10 litres per minute. The dimensions and number of the channels 209 are configured to create a sufficiently large opening to allow communication whilst retaining sufficient positive pressure to at least partially deliver respiratory therapy to the user. This lowers the pressure in the breathing chamber which reduces the effort required by the wearer to exhale, and thus reduces the effort in speaking. The speech valve 203 is located near the centre and front of the patient interface 200 so that the direction of the air flow through the speech valve 204 assists in carrying the sound of the speech in the direction the user is facing, for example, to the addressee of the user.

When the user has finished speaking, the user can relax the pressure applied to the cap 211, allowing the positive pressure in the interior of the breathing chamber to force the plunger 205 in the opposite direction—away from the user's face—towards the forward position. In the forward position the plunger 205 forms a seal with a front part of the barrel 207 and occludes fluid communication between the ambient environment and the channels 209. The pneumatic bias, together with any mechanical bias, biases the plunger 205 towards the forward position. The valve 203 may be arranged such that the positive pressure in the breathing chamber, and the direction of the air flow, provides sufficient bias (without a separate mechanical bias) on the plunger 205 towards the forward position, such that when the user stops pushing the plunger 205 towards their face, or relaxes the pressure they are applying on the plunger 205, the plunger 205 is moved forwards by the force of the air flow into the patient interface and positive pressure.

It will be appreciated by those skilled in the art that embodiments of the speech valve in other geometries are within the scope of the invention. For example, it is envisaged that an embodiment includes a speech valve comprising a barrel having a non-circular cross section, for example an elliptical cross section and complementary elliptical plunger assembly. One advantage of non-circular components in a speech valve is that rotation of the plunger within the barrel is restricted, so specific guiding protrusions and grooves in the barrel and plunger are not necessary. The shape, length and number of channels in the rear section of the barrel may also be varied by the skilled person without departing from the range and scope of the invention. Sharp edges and corners are preferably avoided, however, as the additional noise and turbulence generated can be undesirable.

With reference to FIGS. 13 to 18, a patient interface 300 comprises a speech valve 303 comprising a sealing member comprising a valve flap 305 which rests and seals against an array of speech valve openings 309. The speech valve 303 is provided on the mask body 3, preferably in a central location on the mask body 3. The speech valve comprises a valve body that forms part of the mask body 3. The array of speech valve openings 309 are formed through the mask body in the region of the valve body.

As with the example of FIGS. 6 to 12, in this example the breathable gas inlet 10 and gas wash-out vent 15 are located at opposite ends of a tubular inlet manifold 321 below the speech valve 303, underneath the breathing chamber, and substantially perpendicular to the speech valve 303.

The valve flap 305 is pivotally mounted to the interior of the mask body 3, and in its sealing condition is substantially coterminous or overlapping with the region of the mask body 3 in which the valve openings 309 are located. A first, front surface of the flap 305 rests against the interior surface of the mask body 3, overlapping and occluding the valve openings 309, as can best be seen in FIG. 14. The interior surface of the mask body 3 through which the valve openings 309 are formed is substantially planar. The outer surface of the mask body 3 through which the valve openings 309 are formed is also substantially planar. A lower part of the flap 305 is pivotally mounted at a pivot mount 311 which is moulded into or formed with the interior of the mask body 3 at a location below the valve openings 309. In one embodiment, the mount 311 includes an elongate recess 313 which receives a cylindrical lower part of the flap 305, and about which the flap 305 can rotate.

The breathing gas inlet 10 is provided in a transverse inlet manifold 321 configured to connect with an end connector of a breathing gases conduit which supplies breathing gases from, for example, a flow generator. The inlet 10 comprises an opening facing a lateral side of the mask assembly 302. The manifold 321 comprises an intermediate duct 323 which forms a gas flow path from inlet 10 into the interior of the mask body 3. The intermediate duct 323 is located directly below the speech valve 303. The gas wash-out vent 15 is located at the opposite end of the manifold 321 to the inlet 10.

A protrusion 325 of the flap 305 protrudes through an aperture 326 in the mask body 3 located between the mount 311 and the valve openings 309. The protrusion 325 can be pressed by a user to pivot the flap 305 towards their face, and away from valve openings 309. The exterior outer surface of the protrusion 325 may be textured, tactile-featured, or contain an otherwise indicative feature to help the wearer locate the protrusion 325 by touch.

In the illustrated embodiment, the protrusion has a plurality of buttons that provide the tactile feature.

Biasing of the flap 305 against the interior surface of the mask body 3 is provided by the pneumatic bias of the pressure within the breathing chamber, in combination with mechanical bias provided by a biasing element 327, such that the flap 305 is biased into a closed position in which the valve openings 309 are occluded. The biasing element 327 may be in the form of a living spring comprising an elastically deformable arcuate projection integrally formed with the flap 305 and which extends from its rear surface. A portion of the living spring 327 abuts an internal part of the mask body 3, and in particular abuts part of the inlet manifold 321. As the flap 305 is pivoted rearward from the closed condition, by a user pressing on the protrusion 325, the living spring 327 is deformed, inducing a restoring force within the living spring 327. The restoring force provides a bias on the flap 305 towards the forward position such that when pressure on the protrusion 325 is removed or relaxed, the living spring 327 urges the flap 305 to pivot toward the forward, closed, position, in combination with the above described pneumatic bias.

In an alternative embodiment, the biasing element may comprise any other type of spring, such as a helical or leaf spring to replace the living spring. The spring is connected at one end to the flap 305 and at a second end to a location in the interior of the mask body 3.

The flap 305 is of sufficient thickness and/or rigidity such that the entirety of the flap 305 may be pivoted about the mount 311 by the pressing of the protrusion 325.

In use, during respiratory therapy, when the user wishes to speak more clearly and easily, the user presses the protrusion 325 towards their face using their finger(s). The restoring force of the living spring 327 must be overcome for the user to open the flap 305. In addition, the positive pressure in the interior of the mask body 3 resists the flap 305 being pressed inward, so the user must press sufficiently firmly to overcome this force.

When the flap 305 is pivoted rearward, and away from valve openings 309, the positive pressure inside the mask body 3 causes breathing gases to flow out of the interior of the mask body 3 through the valve openings 309. Pressing the flap 305 further inward causes the flow to increase towards a maximum flow rate determined by the combined size of the valve openings 309 and flow characteristics from the flow generator.

The size of the valve openings 309 are configured to create a sufficiently large opening to allow communication whilst retaining sufficient positive pressure to at least partially deliver respiratory therapy to the user. The flow rate through the valve openings 309 is up to about 60 L/min.

Opening the valve openings 309 opens a flow path from the breathing chamber to atmosphere when the user wishes to speak, and may lower the pressure in the mask assembly which reduces the effort required by the user to exhale, and thus reduces the effort in speaking. When the valve openings 309 are located near the centre and front of the patient interface 100, the direction of the air flow through the valve openings 309 also assists in carrying the sound of the speech in the direction the user is facing, for example, to the addressee of the user.

The position of the inlet manifold 321, and intermediate duct 323 to the rear of and adjacent the flap 305, causes a flow of breathable gas to flow past the rear face of the flap 305 in normal use, when the speech valve 303 is closed. The direction of gas flow from the inlet thus produces a pneumatic bias on the flap 305 towards the closed position.

Figures 19A, 19B:
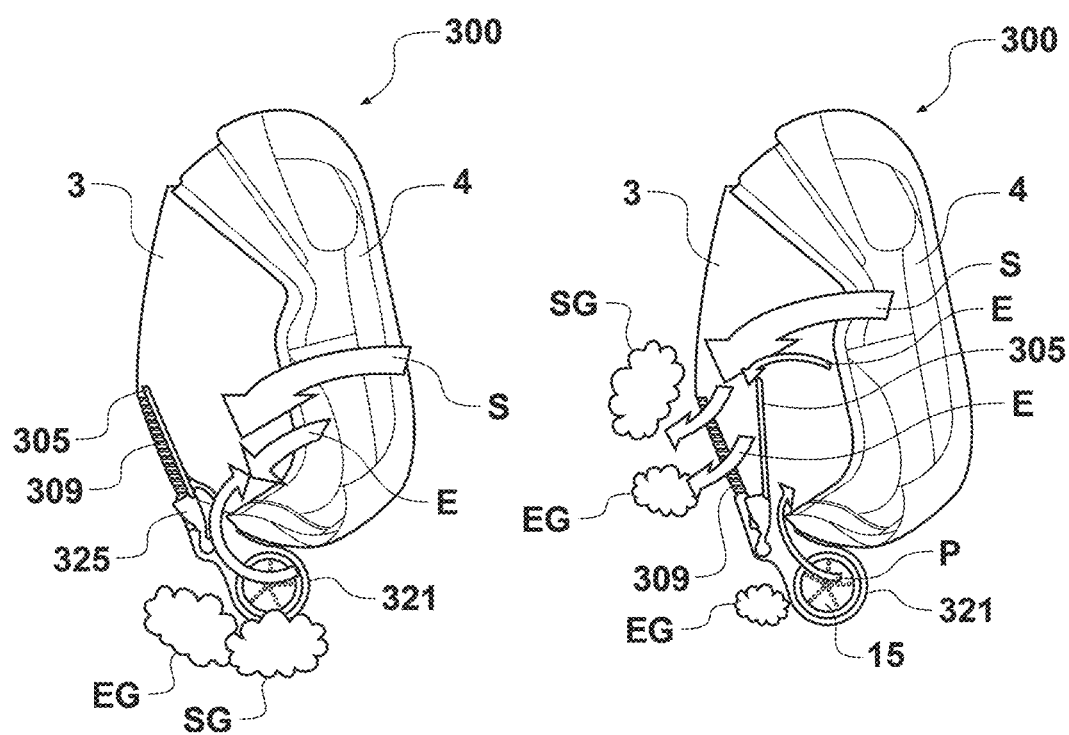
FIGS. 19a and 19b are sectional side views of the assembly of FIGS. 13 to 18 with the speech valve in closed and open conditions respectively.

Pressing the flap 305 backwards at least partially restricts the air flow from the inlet 10 into the mask body 3, which reduces interference between incoming air flow and the exhaled breath, and may reduce the pressure within the breathing chamber. In addition, the location of the inlet 10 is such that the direction of exhaled breath (and therefore speech) is substantially perpendicular to the direction of the incoming air flow from the inlet, which further reduces interference between incoming air flow and exhaled breath. With reference to FIG. 19A, the speech valve 303 is closed, the pressurised gas is indicated by arrow P, exhaled gas by arrow E and exhaled gas EG, and the direction of air flow from speech by arrow S and exhaled speech gas SG. The facilitation of speech when the speech valve 303 is open can be seen with reference to FIG. 19B, with exhaled speech valve S, SG flowing through the speech valve 303, and the inlet pressurised gas P being reduced when the speech valve 303 is open. A relatively small proportion of exhaled gas E exits via gas wash-out vent 15, with the remaining exhaled gas E via speech valve 303.

When the user has finished speaking, the user can relax the pressure applied to the protrusion 325, allowing the positive pressure in the interior of the mask body 3 (assisted by the biasing element) to move the flap 305 in the opposite direction—away from their face—towards the closed position and against the valve openings 309. In the forward, closed position the front surface of the flap 305 forms a seal against and occludes the valve openings 309. The living spring 327 further biases the flap 305 towards the forward position. The living spring 327 may therefore act to initiate movement of the flap 305 towards the forward, closed position, moving the flap 305 to a position in which the flap 305 is better exposed to the pneumatic bias which closes the valve 303.

Figure 20:
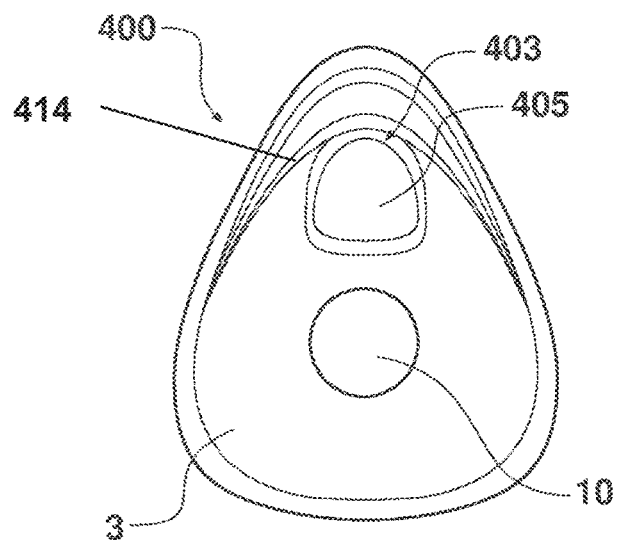
FIG. 20 is a perspective view of a patient interface assembly in accordance with a fourth aspect of the disclosure.
Figure 21:
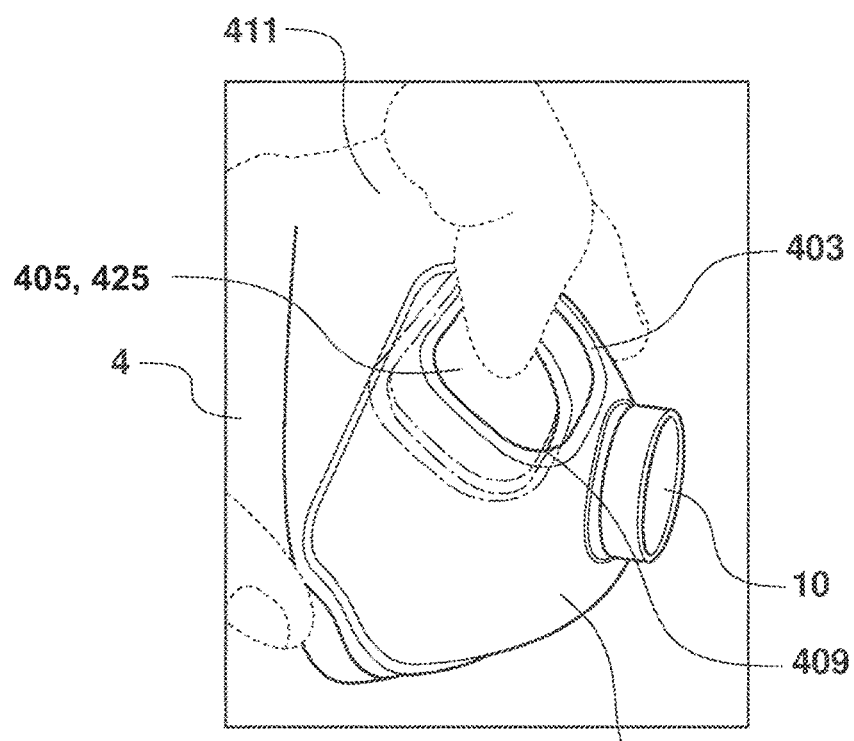
FIG. 21 is an enlarged perspective view of the assembly of FIG. 20 with the speech valve in an open condition.

With reference to FIGS. 20 to 21, a patient interface 400 comprises a substantially centrally located speech valve 403 comprising a sealing member comprising a valve flap 405 which rests and seals against a valve body being a part of the mask body 3 formed with a single speech valve opening 409. In this example, the breathable gas inlet 10 is central on the front of the mask body 3, directly below the speech valve 403 and substantially aligned with the speech valve 403, when viewed from the front. The speech valve 403 in this example is mounted above the inlet 10, adjacent the user's nose.

Valve flap 405 is pivotally mounted to the interior side of the mask body 3, and is substantially coterminous or overlapping with the region of the mask body 3 in which the valve opening 409 are located. The flap 405 comprises a body that fills opening 409 and a peripheral lip or flange that overlays and seals against the interior surface of the mask body 3 about the margin of the opening 409. An upper part of the flap 405 is pivotally mounted on the mask body 3 above the valve opening 409 via a mount 411. The flap 405 could be pivotally mounted at any other location, such as below the valve opening 409. In this embodiment, the mount 411 is integrally formed with the flap 405, the mount 411 and flap 405 being integrally formed from a silicone or other deformable material which is secured to the exterior of the mask body 3, and which may be integral with the seal 4. It will be clear to the skilled person that the mount 411 may be located on an interior or exterior side of the mask assembly, and could be separate to the mask seal 4.

A protrusion 425 of the flap 405 protrudes through the valve opening 409. The protrusion 425 can be pressed by a user to pivot the flap 405 towards their face, and away from valve opening 409. The exterior outer surface of the protrusion 425 may be textured, tactile-featured, or contain an otherwise indicative feature to help the wearer locate the actuator 425 by touch.

The protruding actuator 425 assists the user in finding the actuator 425, as well as improves the rigidity of the flap member 414 and assists in forming a seal with the walls of the vent opening 409.

The valve flap 405 is positioned inside the mask body 3 and seals against the inner edge of the vent opening 409. The valve flap 405 is held in this position during therapy by the internal air pressure.

In order to activate the speech valve, the flap 405 is manually pressed and moved away from the surface of the mask body 3, creating an intentional leak and allowing the patient to communicate more clearly.

The above described embodiments stem from work which indicated that pressure within the patient interface prevents or restricts the outbreath associated with talking, in that air flow is needed to talk, and the air pressure can restricts how much the user can say: broadly, the higher the pressure the less can be easily said. Voice transmission against the air flow can also restrict the clarity of the talking sound in that it can muffle the sound and affect the speech volume. Further, the above work indicates that speech can be better transmitted when the sound waves travel with the flow of air, as opposed to against the direction of the flow of air. The resulting transmitted speech may be louder and clearer to the recipient.

Figure 22:
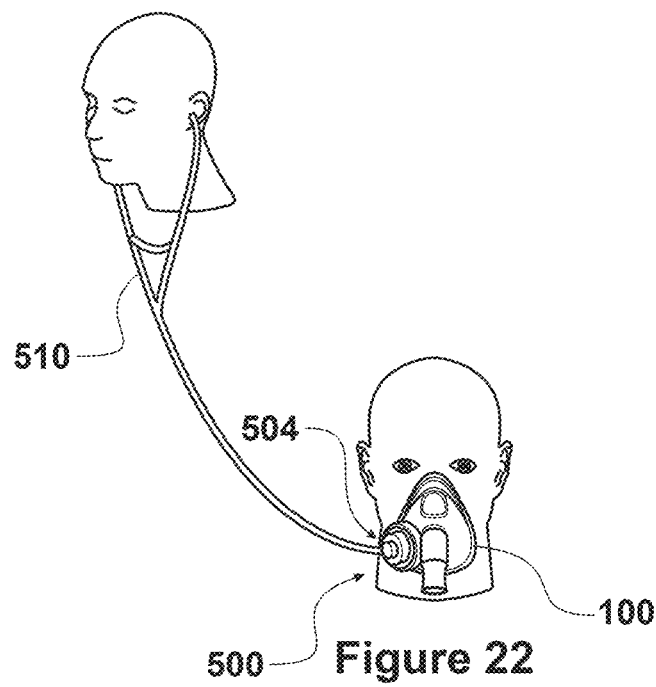
FIG. 22 is a perspective view of a stethoscope and patient interface assembly including a spacer element in accordance with an aspect of this disclosure.
Figure 23:
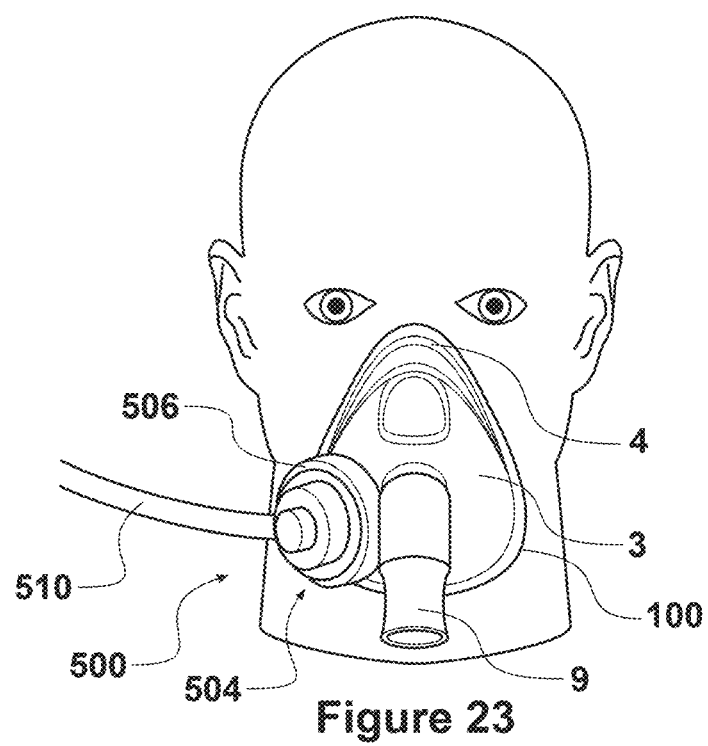
FIG. 23 is an enlarged view of part of the assembly of FIG. 22.

With reference to FIGS. 22 and 23 a stethoscope device 500 is provided for use with a patient interface 100, the stethoscope device comprising a spacer configured to be positioned between the stethoscope and the patient interface, the spacer comprising a body having a first surface arranged to contact an exterior surface of the patient interface, and a second opposing surface arranged to contact a diaphragm of the stethoscope. The spacer body is deformable so as to:
 a) conform to the shape of the exterior surface of the patient interface; and
 b) attenuate or alleviate vibrations of the patient interface from being transferred through the spacer to the stethoscope.

The spacer 504 comprises a first portion 506 of deformable material capable of conforming, on contact, to the shape of the contours of the exterior surface of the patient interface 100 and in particular the mask body 3.

The spacer 504 is disc shaped and has a central opening or bore extending through the disc. At least the first portion 506 comprises a material which is deformable and conforms to the shape of the contours of the exterior of the patient interface 100 and which also dampens vibrations in the patient interface 100 transferring to the stethoscope 510.

The first portion 506 may be mounted or attached to an exterior part of the mask body 3, at a location which is unobstructed by conduits, elbows, apertures or the like, such as to the side of a central passage and elbow assembly. When the patient interface 100 is worn by a user, for example during respiratory therapy, and the user wishes to speak to a stethoscope user medic, the medic contacts the diaphragm of the stethoscope with the spacer 504, and the user then speaks while wearing the patient interface 100.

In an alternative embodiment, the spacer 504 is attachable to the diaphragm of a stethoscope 510 with the first portion 506 exposed such that it may be applied to an exterior surface of the patient interface 100. Preferably, the spacer 504 is removably attachable. When the patient interface 100 is worn by a user, for example during respiratory therapy, and the wearer wishes to speak to a medic, the medic contacts the first portion 506 on the patient interface 100 such that the central opening 512 defines an air gap between the patient interface 100 and the diaphragm, and the user then speaks while wearing the patient interface 100.

The use of the spacer 504 improves the audibility of the user's speech to the clinician by dampening the sound effects created by the patient interface 100 (e.g. resonances in the interior of the mask assembly and vibrations through the mask assembly itself). A function of the spacer is to provide an air gap between the diaphragm and the mask body 3.

The spacer material may be a foam material or materials which will deform to the shape of the mask body 3, as well as damp out vibrations between the mask body 3 and the stethoscope body, resulting in the diaphragm only receiving the feedback as a result of speech resonating in the mask cavity.

Many medics carry stethoscopes with them at all times while on duty. Thus, the provision of the spacer, either with the patient interface 100 or with the stethoscope, enables rapid and simple facilitation of communication with patients wearing a respiratory mask. The spacer provides a relatively cheap and easy method to enable communication with patients while wearing a patient interface 100, and while receiving respiratory therapy.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. Additionally, as used herein, "gradually" has its ordinary meaning (e.g., differs from a non-continuous, such as a step-like, change).

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

The invention claimed is:

1. A patient interface configured to be connected to a respiratory therapy system to deliver a flow of breathable gases to a user, the patient interface comprising:
   a mask body;
   a mask seal secured to the mask body and configured to form a seal with a face of the user, at least around a mouth of the user; the mask body and mask seal being arranged to define an interior breathing chamber of the patient interface;
   an inlet to the breathing chamber configured to receive a flow of breathable gases into the breathing chamber; and
   a user actuatable speech valve operable to selectively occlude and open a speech flow path from the breathing chamber to atmosphere when the user wishes to speak, the speech valve comprising:
      a valve body, the valve body being a region of the mask body surrounding the inlet and comprising at least one vent opening configured to be in fluid communication with the breathing chamber and an ambient environment; and
      a sealing member comprising a sealing disc, the sealing member and the at least one vent opening being configured such that the at least one vent opening can be selectively occluded by the sealing disc.

2. The patient interface of claim 1 wherein the at least one vent opening comprises a plurality of vent openings.

3. The patient interface of claim 1 wherein at least one of the at least one vent opening and the sealing member is movable between a first position in which the sealing member sealingly occludes the at least one vent opening, and a second position wherein the sealing member at least partially opens the at least one vent opening.

4. The patient interface of claim 3 wherein a region of the speech valve is accessible externally of the patient interface and operably connected to the at least one vent opening or the sealing member, the region being accessible to a hand of the user and configured to move at least one of the at least one vent opening and the sealing member between the first and second positions.

5. The patient interface of claim 3 wherein the sealing member is movable between the first and second positions.

6. The patient interface of claim 1 configured to exert a bias on the speech valve to bias the speech valve to occlude the speech flow path.

7. The patient interface of claim 6 wherein the speech valve is exposed to the breathing chamber such that pressure within the breathing chamber exerts a mechanical bias on the speech valve.

8. The patient interface of claim 6, further comprising biasing means configured to exert a bias, or a further bias, on the speech valve to bias the speech valve to occlude the speech flow path, the biasing means being selected from any one or more of:
  a mechanical biasing means;
  a magnetic biasing means; or
  an electro-mechanical biasing means.

9. The patient interface of claim 1, wherein at least part of the speech valve is exposed to the interior of the breathing chamber such that pressure within the breathing chamber exerts a pneumatic bias on the speech valve to bias the speech valve to occlude the speech flow path.

10. The patient interface of claim 1 wherein the at least one vent opening is provided at the inlet to the breathing chamber, and further wherein the patient interface comprises a conduit connector configured to connect a breathing gas delivery conduit to the inlet to the breathing chamber, the sealing member being coupled to the conduit connector, wherein the conduit connector and the sealing member are configured to be movable relative to the inlet to open and occlude the at least one vent opening.

11. The patient interface of claim 10 wherein the conduit connector and the sealing member are configured to be movable in a direction of a longitudinal axis of the inlet.

12. The patient interface of claim 10 wherein the sealing member is positioned inside the breathing chamber.

13. The patient interface of claim 10, wherein the sealing member extends radially outwardly from a tubular part of the conduit connector that extends through the breathing gas inlet.

14. The patient interface of claim 10, wherein the conduit connector comprises an elbow connector attached to, or configured to be attached to, a distal end of the breathing gas delivery conduit.

15. The patient interface of claim 10, wherein the inlet comprises an inlet aperture, and the at least one vent opening comprises a plurality of vent openings arranged around a perimeter of the inlet aperture.

16. The patient interface of claim 15, wherein the conduit connector and the inlet aperture are configured to engage with any one of:
  a friction fit; or
  a sliding fit.

17. The patient interface of claim 1, wherein the speech valve is located adjacent the mouth of the user when the patient interface is mounted on the user.

18. The patient interface of claim 1 where the speech valve is in direct fluid communication with the inlet to the breathing chamber of the patient interface.

19. The patient interface of claim 1 comprising a plurality of rows and/or columns of vent openings.

20. The patient interface of claim 1, wherein the patient interface is any one of:
  an oral mask configured to seal around the mouth of the patient; or
  a full face mask configured to seal around both the mouth and nose of the patient.

* * * * *